United States Patent
Jean et al.

(10) Patent No.: US 11,415,267 B2
(45) Date of Patent: Aug. 16, 2022

(54) SYSTEM AND METHOD FOR DIAGNOSING A CONDITION OF AN ENGINE

(71) Applicant: PRATT & WHITNEY CANADA CORP., Longueuil (CA)

(72) Inventors: Maurice Jean, Morin-Heights (CA); Nathalie Savard, St-Jean-sur-Richelieu (CA); Sonia Sevigny, Brossard (CA); Stephanie Pronovost, Chambly (CA)

(73) Assignee: PRATT & WHITNEY CANADA CORP., Longueuil (CA)

( * ) Notice: Subject to any disclaimer, the term of this patent is extended or adjusted under 35 U.S.C. 154(b) by 672 days.

(21) Appl. No.: 16/439,154

(22) Filed: Jun. 12, 2019

(65) Prior Publication Data

US 2020/0393082 A1    Dec. 17, 2020

(51) Int. Cl.
   *F16N 29/04*  (2006.01)
   *F01D 21/00*  (2006.01)
   *F01D 25/18*  (2006.01)
   *G01N 33/28*  (2006.01)

(52) U.S. Cl.
   CPC .......... *F16N 29/04* (2013.01); *F01D 21/003* (2013.01); *F01D 25/18* (2013.01); *G01N 33/2888* (2013.01); *F05D 2260/80* (2013.01); *F05D 2270/11* (2013.01)

(58) Field of Classification Search
   CPC ..... G01N 21/17; G01N 21/1702–1717; G01N 2021/1706–1744; G01N 33/2888; F16N 29/02; F16N 29/04; F01D 21/003; F01D 25/18; F05D 2260/80; F05D 2270/11
   See application file for complete search history.

(56) References Cited

U.S. PATENT DOCUMENTS

| 8,676,436 | B2  |   | 3/2014  | Raimarckers et al. |
| 9,188,577 | B2  | * | 11/2015 | Yepez ................. G01N 33/2888 |
| 2012/0225489 | A1 | * | 9/2012 | Yepez ..................... G01V 9/007 |
|  |  |  |  | 436/139 |

(Continued)

FOREIGN PATENT DOCUMENTS

| RU |      | 2182330 C2 * | 5/2002 |  |
| WO | WO-2020002946 A1 * | 1/2020 | ......... B01D 11/0496 |

OTHER PUBLICATIONS

Rossman, A. 22.3.4 Monitoring of the oil and so of the oil system. Aeroengine Safety. Graz University of Technology. Retrieved from https://aeroenginesafety.tugraz.at/doku.php?id=22:223:2234:2234 on Mar. 24, 2022. (Year: 2022).*

(Continued)

*Primary Examiner* — Topaz L. Elliott
(74) *Attorney, Agent, or Firm* — Norton Rose Fulbright Canada LLP

(57) ABSTRACT

There is provided a method and system for diagnosing a condition of an aircraft engine. The method comprises obtaining a sample of lubricating fluid from the engine, filtering the sample to obtain a plurality of particles from the lubricating fluid, directing an excitation beam towards the particles, detecting an energy level emitted from the particles in response to the excitation beam, determining a level of coking in the lubricating fluid based on a difference between the energy level as detected and an expected energy level, and diagnosing a condition of the engine based on the level of coking in the lubricating fluid.

18 Claims, 7 Drawing Sheets

(56) References Cited

U.S. PATENT DOCUMENTS

| | | | |
|---|---|---|---|
| 2016/0230589 A1 | 8/2016 | Debbouz et al. | |
| 2016/0370341 A1 | 12/2016 | Jean et al. | |
| 2017/0038311 A1* | 2/2017 | Conrad | G01N 33/2888 |
| 2018/0364120 A1* | 12/2018 | Ribarov | G01N 29/4436 |
| 2019/0063678 A1 | 2/2019 | Ganiger et al. | |
| 2019/0072536 A1 | 3/2019 | Jean | |
| 2021/0381641 A1* | 12/2021 | Nitsche | G01J 3/10 |

OTHER PUBLICATIONS

Rossman, A. 22.3.2 Oil Coking. Aeroengine Safety. Graz University of Technology. Retrieved from https://aeroenginesafety.tugraz.at/doku.php?id=22:223:2232:2232 on Mar. 24, 2022. (Year: 2022).*
Extended European Search Report dated Oct. 13, 2020 in counterpart EP application.

* cited by examiner

SYSTEM AND METHOD FOR DIAGNOSING A CONDITION OF AN ENGINE

TECHNICAL FIELD

The present disclosure relates generally to methods and systems for diagnosing a condition of an engine, for example based on a level of coking in a lubricating fluid.

BACKGROUND OF THE ART

The analysis of engine oil or other lubricant for the purpose of identifying premature component wearing has been performed for several decades using optical atomic spectroscopy (e.g., atomic emission spectroscopy (AES), as well as atomic absorption spectroscopy (AAS)). This technology was the basis for the military aviation's Spectroscopic Oil Analysis Program (SOAP). However, it has certain disadvantages, such as a lack of repeatability among different equipment and an inability to analyze particles greater than 5 µm in diameter. Furthermore, optical atomic spectroscopy is an elemental analysis of the total oil sample and typically does not characterize individual particles in the sample.

Other approaches have since been proposed, whereby individual particles may be characterized and classified based on their chemical composition. However, these approaches do not allow the detection of certain phenomenon in engine oil, such as oil coking.

Therefore, improvements are needed.

SUMMARY

In accordance with a first broad aspect, there is provided a method for diagnosing a condition of an aircraft engine. The method comprises obtaining a sample of lubricating fluid from the engine, filtering the sample to obtain a plurality of particles from the lubricating fluid, directing an excitation beam towards the particles, detecting an energy level emitted from the particles in response to the excitation beam, determining a level of coking in the lubricating fluid based on a difference between the energy level as detected and an expected energy level, and diagnosing a condition of the engine based on the level of coking in the lubricating fluid.

In accordance with another broad aspect, there is provided a system for diagnosing a condition of an engine. The system comprises at least one processor and a memory having stored thereon program code executable by the at least one processor for directing an excitation beam towards a plurality of particles filtered from a sample of lubricating fluid obtained from the engine, determining a level of coking in the lubricating fluid based on a difference between the energy level as detected and an expected energy level, and diagnosing a condition of the engine based on the level of coking in the lubricating fluid.

In accordance with yet another broad aspect, there is provided a non-transitory computer readable medium having stored thereon program code executable by a processor for carrying out the methods described herein.

BRIEF DESCRIPTION OF THE DRAWINGS

Further features and advantages of the present invention will become apparent from the following detailed description, taken in combination with the appended drawings, in which.

It will be noted that throughout the appended drawings, like features are identified by like reference numerals.

DETAILED DESCRIPTION

Coke is the solid residue created when oil undergoes severe oxidative and thermal breakdown at high engine temperatures. While temperature is a main factor in causing oil coking in aircraft engines, the presence of catalysts such as aluminum is also a factor.

There are described herein methods and systems for determining a level of coking in a lubricating fluid of an engine. These methods and systems may be used for engine diagnostics, in particular for gas turbine engines. In some embodiments, the methods and systems described herein may be used for determining a source of coking in an engine, and output a recommendation for engine maintenance and/or diagnosis as a function of the source of coking.

Figure 1:
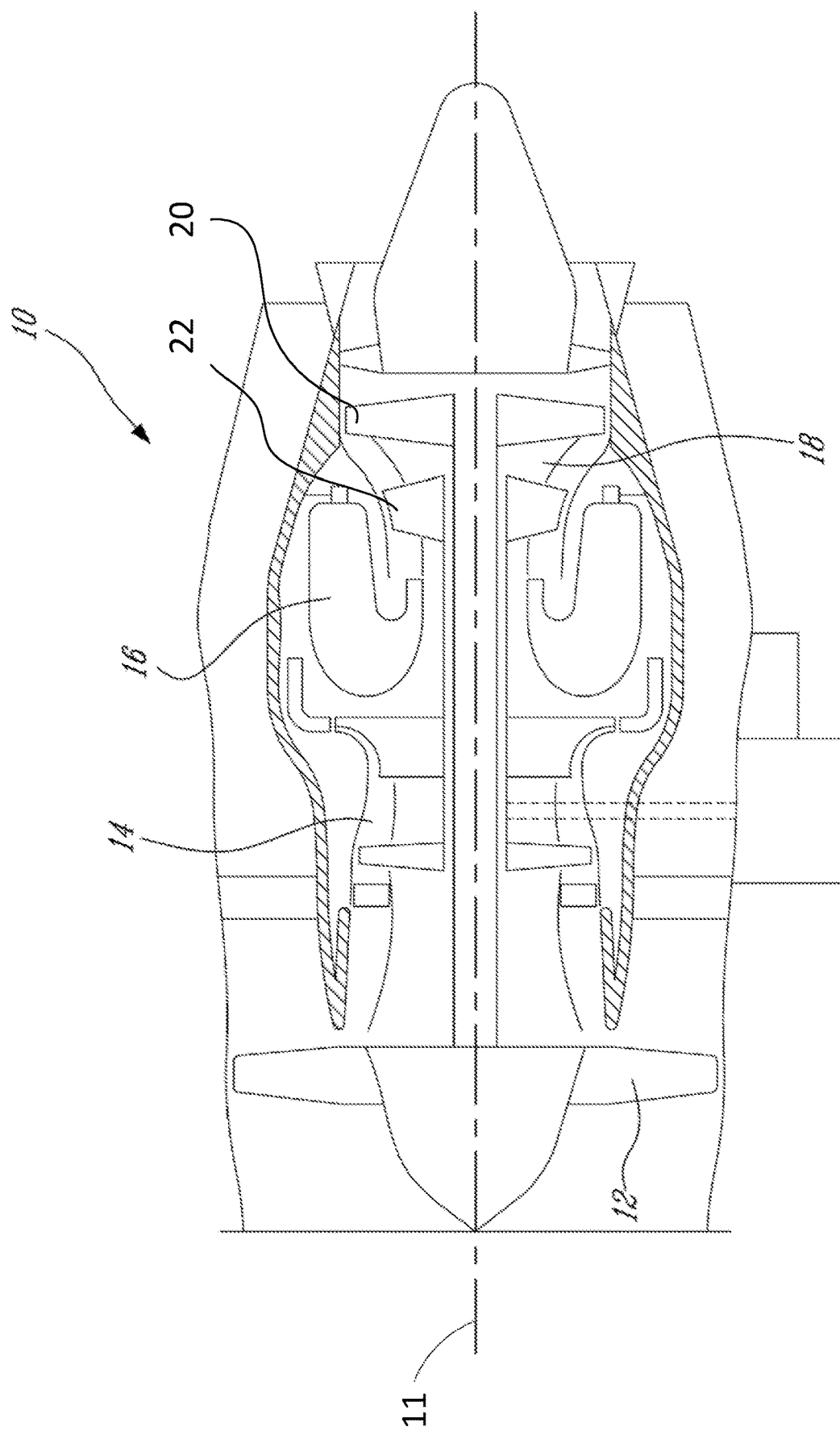
FIG. 1 illustrates an example of a gas turbine engine, in accordance with some embodiments.

FIG. 1 illustrates an example of a gas turbine engine 10 to which the methods and systems described herein may be applied. Note that while engine 10 is a turbofan engine, the methods and systems described herein may be applicable to turboprop, turboshaft, and other types of gas turbine engines. Engine 10 generally comprises in serial flow communication: a fan 12 through which ambient air is propelled, a compressor section 14 for pressurizing the air, a combustor 16 in which the compressed air is mixed with fuel and ignited for generating an annular stream of hot combustion gases, and a turbine section 18 for extracting energy from the combustion gases. Axis 11 defines an axial direction of the engine 10. In some embodiments, a low pressure spool is composed of a low pressure shaft and a low pressure turbine 20. The low pressure shaft drives the fan 12. A high pressure spool is composed of a high pressure turbine 22 attached to a high pressure shaft, which is connected to the compressor section 14.

In some embodiments, the disclosed methods and systems may provide diagnostic and analytical tools based on analysis of particles in fluids, such as engine oil or other lubricants and may provide advance detection of premature wear on specific engine parts and/or detection of failure mechanisms. In some embodiments, the disclosed methods and systems may be suitable for failure prediction for gas turbine engines operating in the field. The disclosed methods and systems may be used for prediction of other wear events including prediction of events other than failure using analysis of any suitable lubricating fluid of the engine. The disclosed methods and systems may also be used to detect any abnormal behavior of an engine component in contact with a lubrication fluid system, for example.

Figure 2:
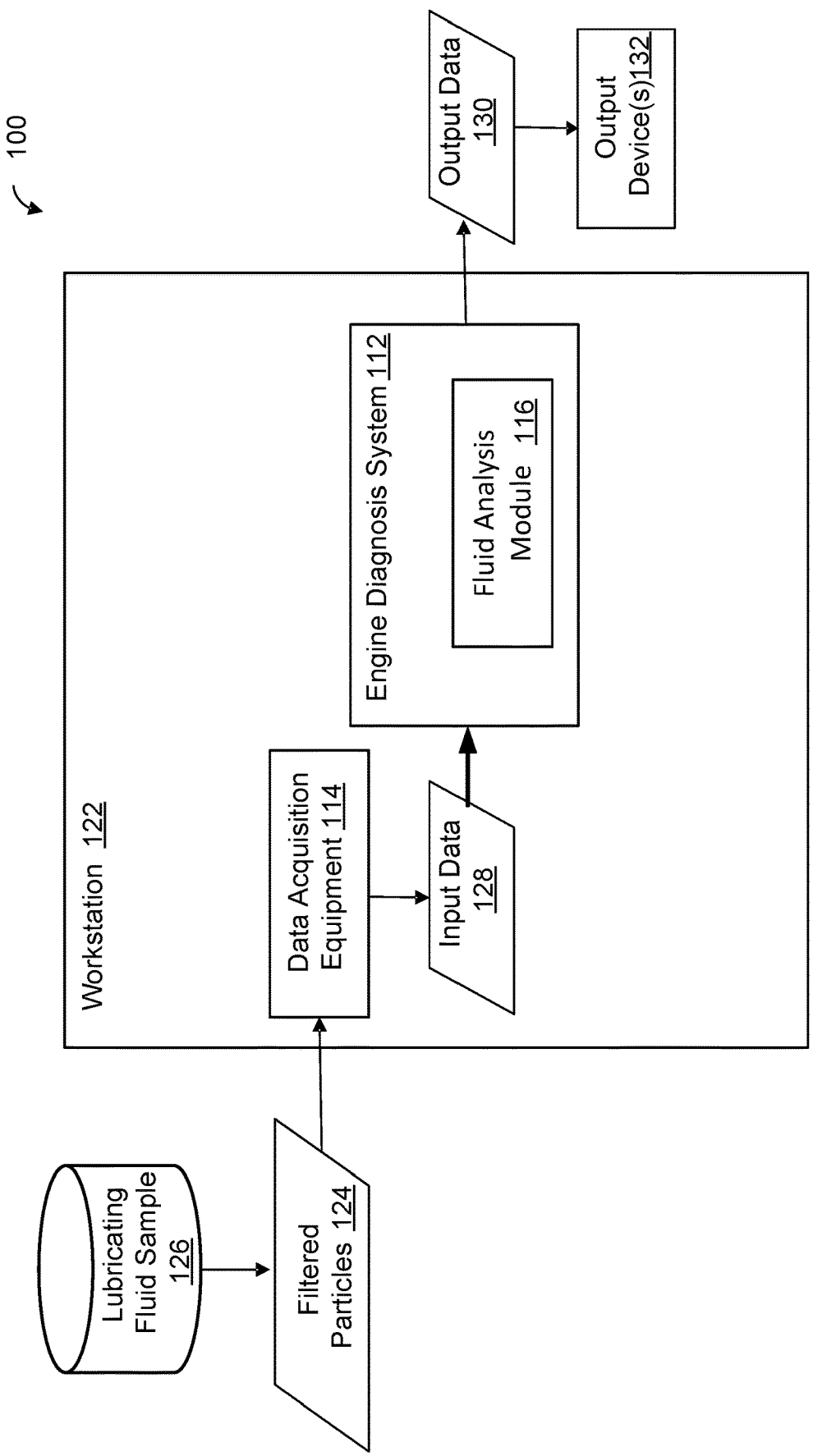
FIG. 2 is a block diagram of an example system for diagnosing a condition of an engine, in accordance with some embodiments.

FIG. 2 is a schematic diagram of an exemplary system 100 for diagnosing a condition of an engine such as the engine 10 and which uses a fluid for lubricating some of its components, such as bearings. System 100 comprises an engine diagnostic system 112 and suitable data acquisition equipment 114 of known or other type. The engine diagnosis system 112 may comprise one or more fluid analysis modules 116, such as a fluid analysis module configured to determine a level of coking in a fluid sample. In some embodiments, a separate fluid analysis module 116 is provided to determine the level of each one of a plurality of materials that may be found in a lubricating fluid.

The engine diagnosis system 112 and data acquisition equipment 114 may be considered part of a workstation 122, such as for example a Scanning Electron Microscope (SEM). Accordingly, data acquisition equipment 114 may comprise an SEM and other related devices, although any other suitable devices/methods for extracting the relevant information from particles 124 filtered from lubricating fluid sample 126 may be used. In some embodiments, data acquisition equipment 114 may comprise an SEM and an X-Ray Fluorescence (XRF) detector for carrying out particle analysis. In some embodiments, the data acquisition equipment 114 may comprise an SEM and an energy dispersive x-ray detector for carrying out particle analysis. In some embodiments, an automated SEM is used and may not require the presence of a human to select the particle(s) 124 that will be analyzed. In some embodiments, software and/or hardware included in workstation 122 may automatically recognize the presence of a particle 124 and may then automatically move a stage and/or an electron beam to the particle(s) 124 on which to perform the analysis.

System 100 may be used to conduct analysis of particles 124 filtered from lubricating fluid sample 126. Data acquisition equipment 114 may be used to analyze filtered particles 124 and generate input data 128. Input data 128 may be processed using engine diagnosis system 112 in order to generate output data 130. In some embodiments, output data 130 may be representative of a diagnosis of the condition of the engine and may be delivered to a user of system 100 or other authorized party via output device(s) 132 (e.g., one or more screens and/or printers) for displaying and/or otherwise providing a report of the result(s) of the diagnosis. System 100 may include one or more input devices (e.g., keyboard and mouse) for receiving user input, as well as one or more data ports and/or communication ports for receiving and/or transmitting data (e.g., wirelessly or through wired connections) from/to other processors, systems and/or devices. Processing of input data 128 by engine diagnosis system 112 may make use of reference data for comparison purpose. It is understood that processing of input data 128 may be performed using one or more processors external to workstation 122.

Figure 3A:
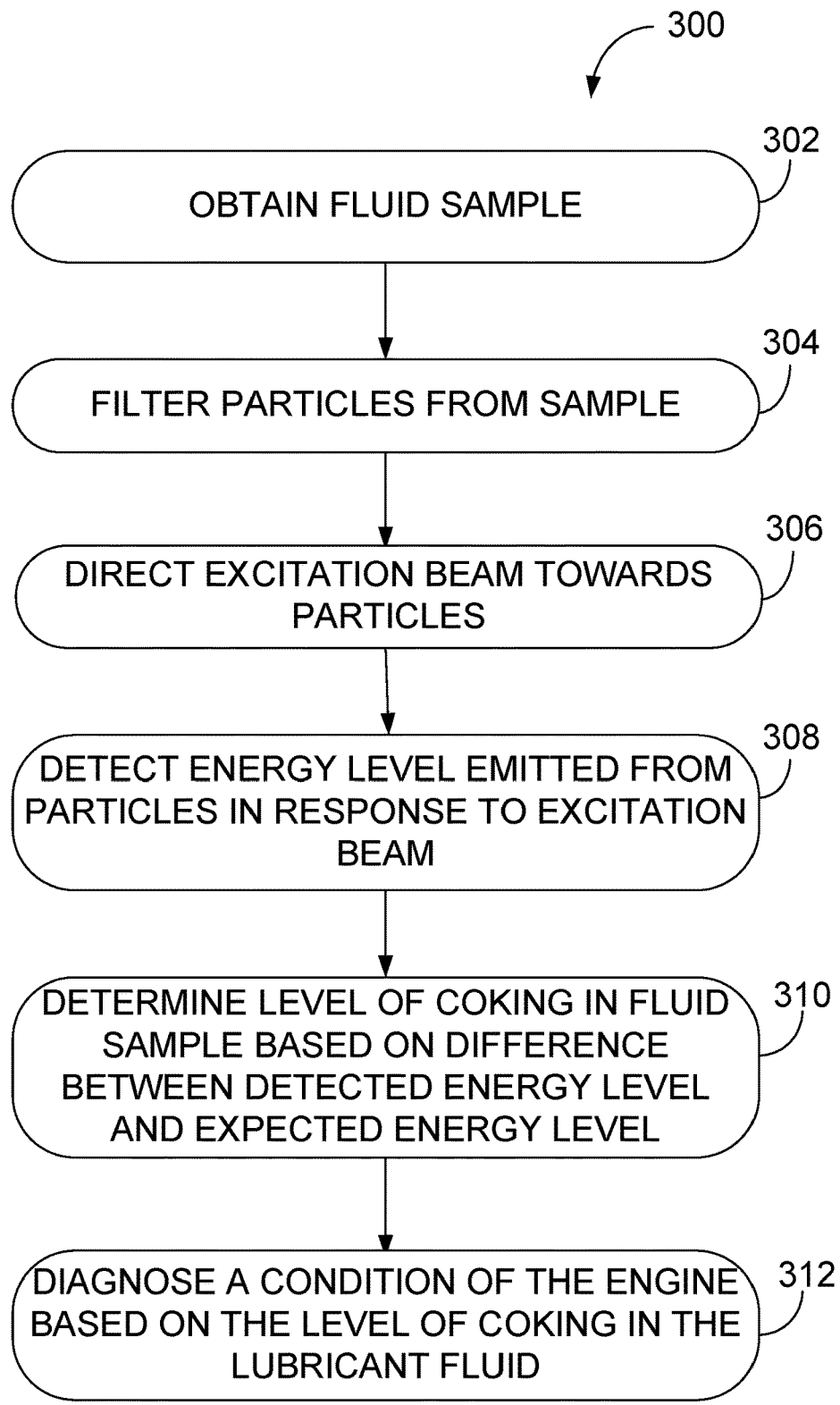
FIG. 3A is a flowchart of an example method for diagnosing a condition of an engine, in accordance with some embodiments.

Referring to FIG. 3A, there is illustrated a flowchart of an example method 300 for diagnosing a condition of an engine, such as engine 10. At step 302, a sample of lubricating fluid is obtained. For example, a sample of oil is obtained from the engine under diagnosis. In the case of a fluid sample from an aircraft engine, the fluid sample may be collected by an aircraft operator. More than one sample may be obtained. The amount of fluid sample obtained (e.g., 25 mL or less) may be selected in order to obtain a certain number of particles. For example, it may be known or expected that a given engine should have a certain density of particles in the fluid after a certain number of operating hours. The volume of fluid sample obtained may thus be determined in order to obtain an optimal quantity of particles. The frequency of sampling may be determined based on the operating hours per year, the maturity of the engine, the typical behavior of the engine type and/or the history of unscheduled engine removal for that engine type, for example. Any known or other engine fluid sampling method may be used, such as but not limited to pressurized line sampling, drop tube sampling, and drain port sampling.

At step 304, the sample of fluid is filtered to obtain a plurality of particles from the sample. Filtering may be performed using various techniques. For example, a collected fluid sample may be filtered using a very fine filter, such as a 0.22 µm filter, in order to filter out even very small particles (e.g., particles sized as small as 0.5 µm in diameter or smaller). Using such a filter, a sample of about 25 mL may produce a surface sample of about 16 mm in diameter. The particles obtained may range in size from about 0.5 µm to about 1600 µm, for example, although smaller or larger particles may also be obtained. The volume of fluid sample filtered and the size of the sample prepared may vary, such as according to the number of particles in the fluid. The volume of fluid sample that is filtered may be determined based on the type of engine and/or the expected normal levels of particles in the fluid. In some examples, the obtained density of particles may be 500 particles per $mm^2$. Other densities may also be used.

At step 306, an excitation beam is directed towards the particles obtained from the sampling of step 304. The particles are thus imaged and input data is generated from the imaging procedure. At step 308, an energy level emitted from the particles in response to the excitation beam is detected. For example, energy dispersive x-rays (EDX), electrons, protons, light, or other electromagnetic radiation may be used as the excitation beam and photons or electrons as the emitted energy. A greater number of photons or electrons are emitted by a particle with a greater surface area than a particle with a smaller surface area. Any imaging technology where the energy level detected in response to excitation is a function of the size of the particle may be used. The energy level detected forms part of the input data. In some embodiments, the input data also comprises a set of peaks along an electromagnetic emission spectrum, for spectroscopic analysis.

In some embodiments, one or more features of the particles are determined based on the input data generated from the imaging procedure. In some embodiments, the features include a respective chemical composition for the particles. In some embodiments, the features include respective geometric parameters for the particles.

In some embodiments, more than one imaging technique is used to generate the input data used obtain the features of the particles. For example, optical imaging may be used to determine geometric parameters of the particles and EDX spectroscopy may be used to obtain the chemical composition. Any other suitable imaging technique may also be used. The two or more imaging procedures may be performed at the workstation 122 using the data acquisition equipment 114. Alternatively, one imaging procedure is performed at a first workstation 122 using first data acquisition equipment 114 and another imaging procedure is performed at a second workstation using second data acquisition equipment.

A subset of the particles (e.g., 10% or less) may be analyzed to determine the features while ensuring a good representation of the whole sample is captured. The analysis of the subset may be normalized to reflect the result for the full sample. For an average fluid sample, about 1500 to 2000 particles may be analyzed. Suitable image analyzer software, such as those conventionally used with SEM, may be used to collect data about particle composition. Analysis of each particle may produce a respective set of data for that particle, for example there may be up to 70 data points for each particle, the data describing various features of the particle (e.g., size, shape and composition, among others).

At step 310, a level of coking in the fluid sample is determined based on a difference between the detected energy level and an expect energy level. Indeed, although carbon deposits resulting from coking cannot be measured directly in the lubricating fluid using standard imaging techniques, a quantity of material resulting from coking may be estimated from the input data generated by the imaging. Coking causes a certain amount of carbon to cover a surface of a given particle. When a carbon-covered particle is imaged using an excitation source, such as an x-ray beam or an electron beam, the carbon blocks a portion of the particle from emitting a signal in response to the excitation. There is a relationship that exists, for fine particles (e.g.: ≤5 µm) that are metallic and/or mineral based, between the geometric parameters of the particle, the chemical composition, and the energy level detected upon excitation from a source. The effect of having such a particle covered in-part by carbon is that the detected energy level will be lower than an expected energy level.

Figure 3B:
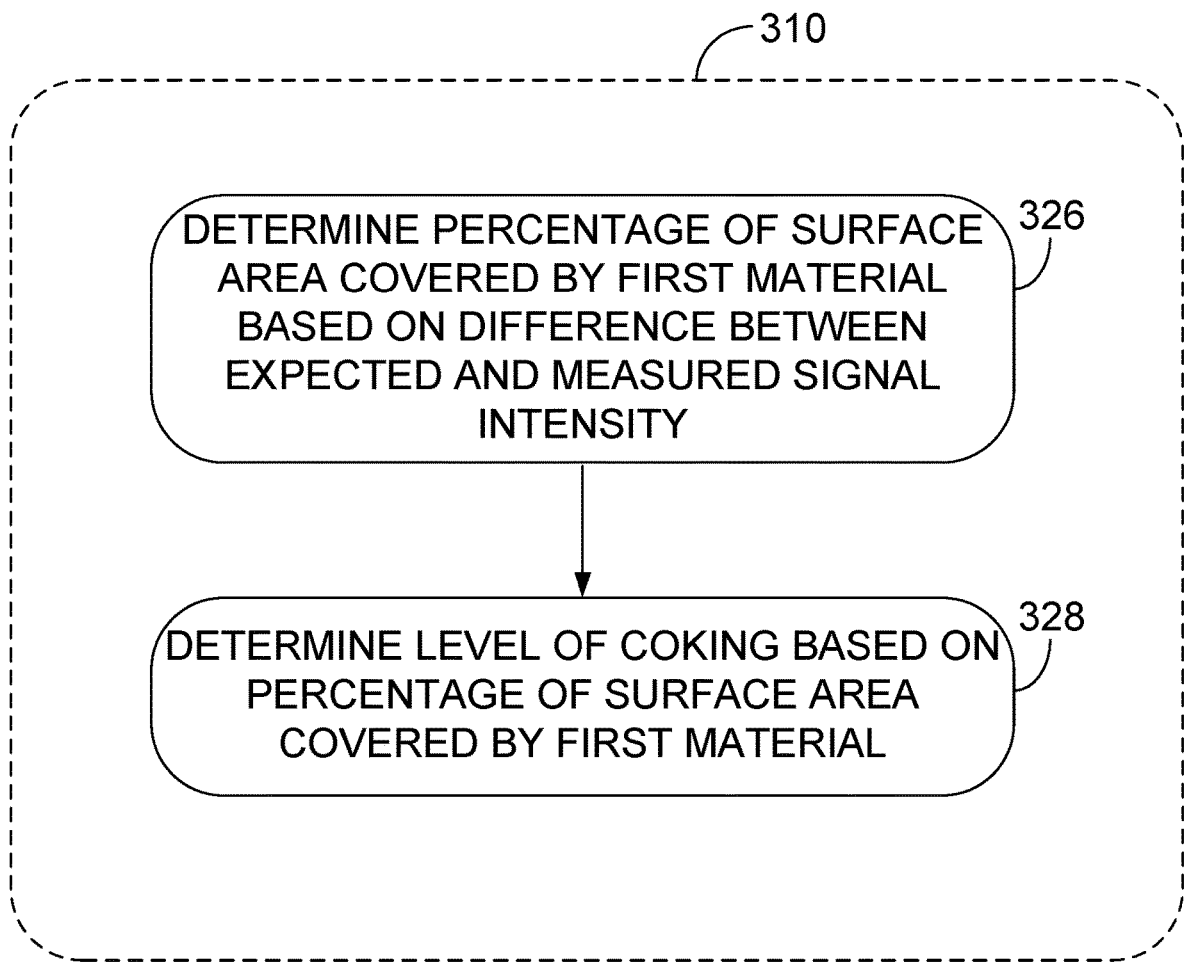
FIG. 3B is a flowchart of an example method for determining a level of coking in a sample of lubricating fluid, in accordance with some embodiments.

Referring to FIG. 3B, there is illustrated an example embodiment for step 310 of determining the level of coking in the fluid sample based on the difference between the expected energy level and the detected energy level, as obtained during the image procedure. As stated above, there exists a relationship between the expected energy level, the chemical composition, and the area of a particle. The relationship is expressed generally as:

$$Q_e = f(\text{chemical composition, Area}),$$

The specific relationship may be determined experimentally for a given chemical composition by measuring the energy level of a particle having substantially 100% of its surface covered by the given chemical composition, for varying surface areas. The expected energy level $Q_e$ is compared to a detected energy level $Q_m$ to obtain a difference in energy levels $Q_\Delta$:

$$Q_\Delta = Q_e - Q_m$$

At step 326, the difference in energy levels $Q_\Delta$ is used to determine a percentage of surface area $S_1$ of the respective ones of the particles covered by a first material, the first material resulting from coking:

$$\frac{Q_\Delta}{Q_e} \cong \frac{S_1}{100}$$

In some embodiments, the first material $S_1$ is carbon. In some embodiments, the first material $S_1$ is a carbon-rich material having other elements, such as hydrogen, Nitrogen, Sulfur, Volatile Matter, moisture, ash, and/or heavy metals. In some embodiments, the first material $S_1$ is defined in accordance with a given composition of the lubricating fluid of the engine, for example by running tests at high temperatures with known catalysts to cause a coking effect.

At step 328, the percentage of surface area $S_1$ of the respective ones of the particles covered by the first material may be used to determine the level of coking in the lubricating fluid.

Figure 4A:
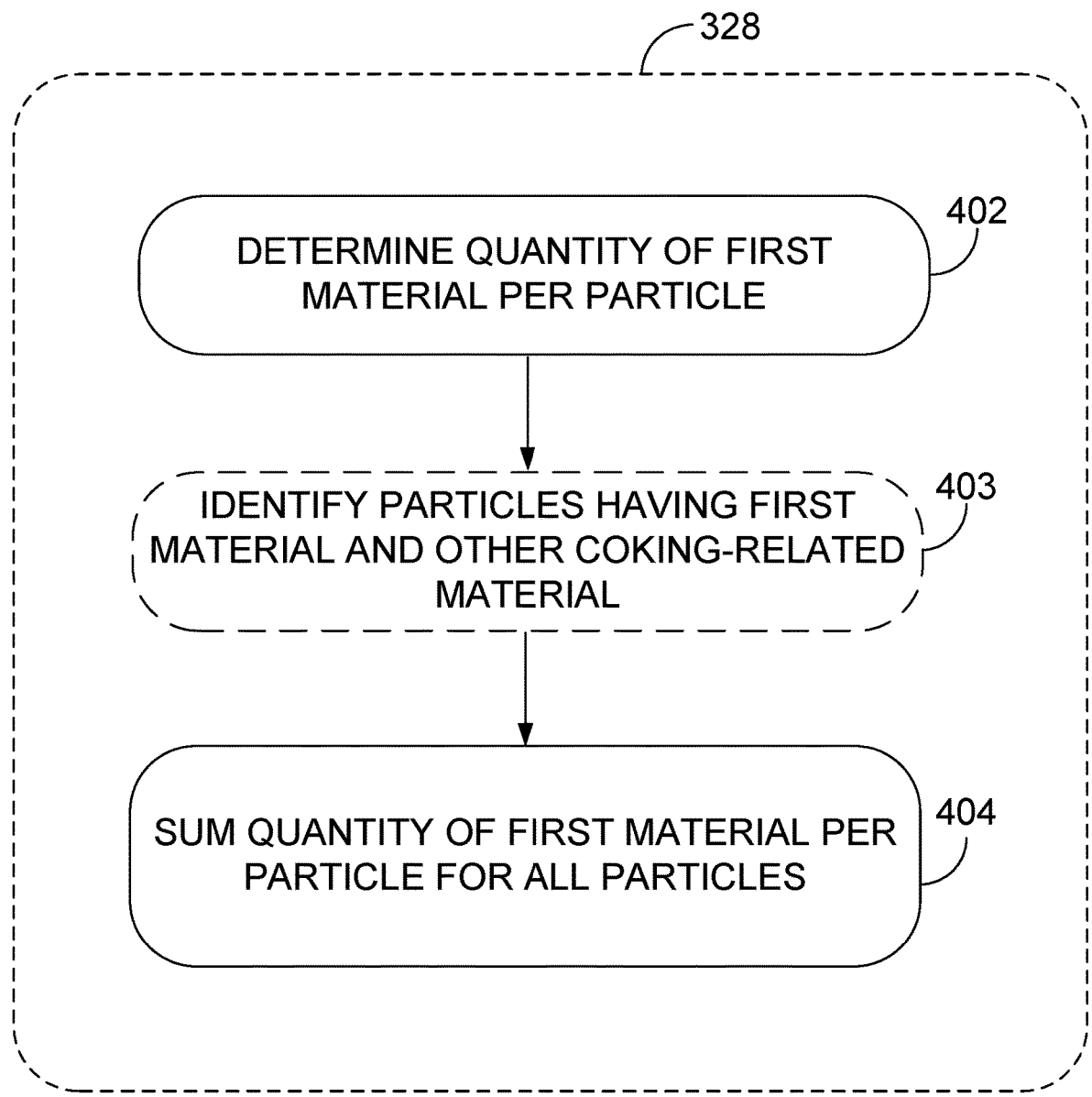
FIG. 4A is a flowchart of an example embodiment for a step of FIG. 3B.

In some embodiments, step 328 is implemented as per FIG. 4A, whereby a quantity of the first material is determined per particle ($M_{1_i}$) at step 402, and the quantity of the first material per particle is summed at step 404, for all particles having the first material, where i=1 to n particles:

$$\text{Coking}\left(\frac{\text{mg}}{\text{L}}\right) = \frac{\sum_{i=1}^{n} M_{1_i}}{V_s} \times 1000$$

$V_S$ is the volume (in mL) of the fluid sample analyzed. Although provided in mg/L, the mass of the first material may be obtained in other units, such as g/L or g/mL, as will be readily understood. In some embodiments, the mass of the first material is used as a level of coking. In some embodiments, a proportional relationship is made between the mass of the first material and the level of coking in the lubricating fluid.

In some embodiments, only a subset of the particles from the sample will comprise the first material. For the other particles, the value for $S_1$ will be set to zero and the result for $M_1$ will also be zero.

In some embodiments, the method 328 in FIG. 4A further comprises a step 403 of identifying which ones of the particles comprising the first material also comprise another material also associated with coking. This step is used, for example, to eliminate carbon particles from sources other than coking, such as from burning rubber or from carbon-made components in the engine. This step may be omitted when the chemical composition of $S_1$ differs from other carbon-rich particles that may be found as residue in the lubricating fluid. The other material also associated with coking may be an additive for the lubricating fluid, such as phosphorous, sulfur, and the like.

Figure 4B:
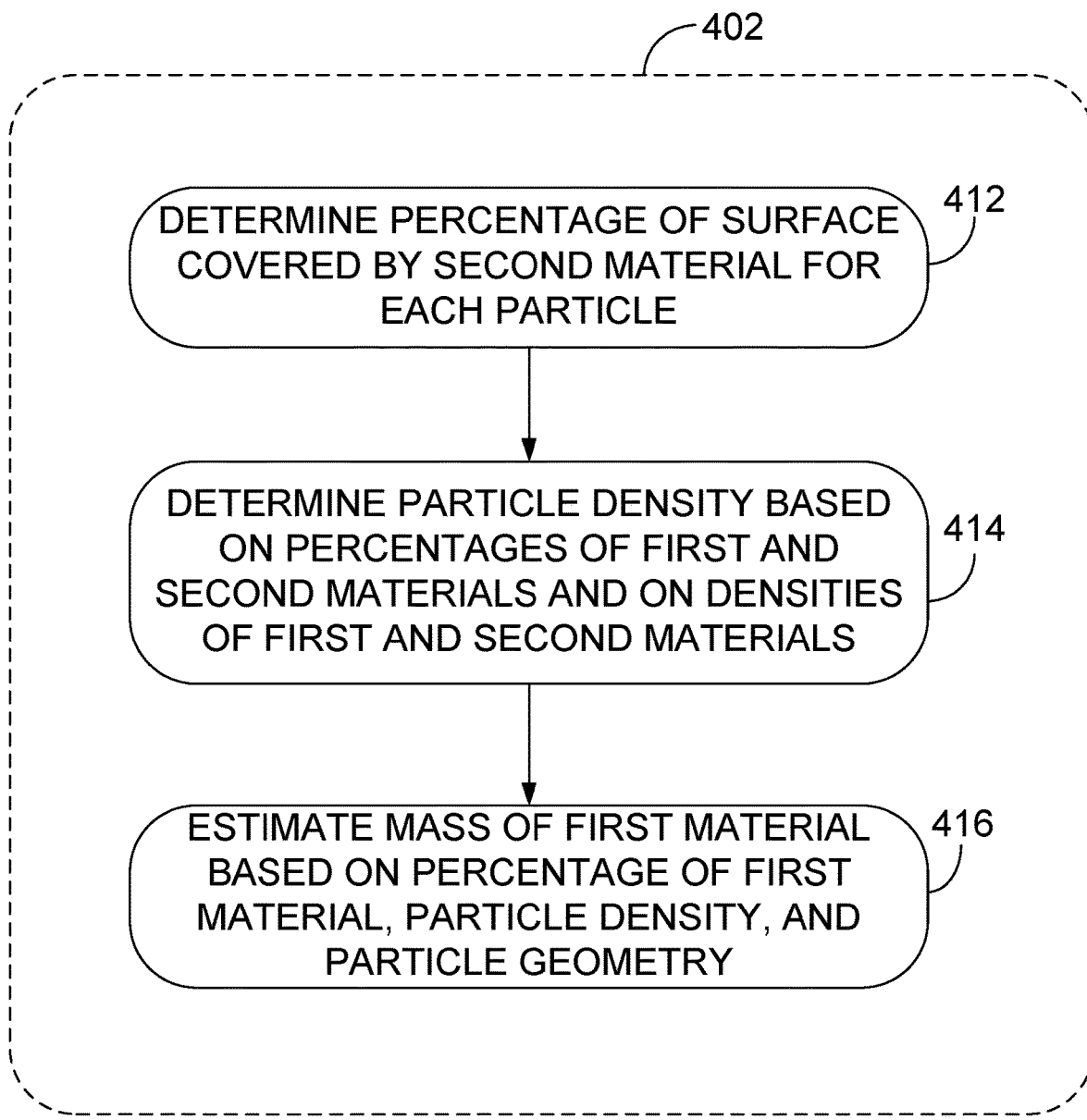
FIG. 4B is a flowchart of an example embodiment for a step of FIG. 4A.

When determining the quantity of the first material per particle, various mathematical steps may be performed once the percentage of surface area of the particle covered by the first material is known. An example embodiment is shown in FIG. 4B. Other embodiments may also apply.

At step 412, the percentage of surface area covered by at least one second material is determined using the input data generated by the imaging, and more specifically using the chemical composition identified per particle (for example by spectroscopy). Grouping all of the elements found on the surface area of the particle together as a single alloy, the following may be used:

$$100\% = S_1 + S_2$$

$S_2$ represents the surface of the particle covered by the at least one second material. The value for $S_1$ is as determined above using the differences in energy levels between what is expected and what is measured. The value for $S_2$ may be measured using, for example, the data acquisition equipment 114 of the workstation 122. In some embodiments, the surface of the particle is covered by two or more second materials. In such cases, the equations used herein may be adapted accordingly.

At step 414, the particle density is determined based on the percentages of the first and second materials, and on the densities of the first and second materials:

$$D_p = \frac{S_1}{100} \times D_1 + \frac{S_2}{100} \times D_2$$

$D_1$ and $D_2$ are the densities of the first and second materials, respectively, and $D_p$ is the density of the particle. The density $D_1$ is a known value associated with the specific chemical composition for the first material, i.e. carbon or a carbon-rich material having other elements therein. The density $D_2$ may be estimated based on the chemical composition of the at least one second material, as measured.

At step 416, the mass of the first material for the particle is determined based on the percentage of surface area of the particle it covers, the density of the particle, and the particle geometry. An estimated volume of the particle $V_p$ may be found using:

$$V_p = \frac{\text{Area} \times \text{smallest dimension} \times 3}{4}$$

The Area corresponds to the total surface area of a particle, such as 10 μm for a particle having dimensions of 2 μm×5 μm. The smallest dimension corresponds to the smallest of the two dimensions forming the Area, for example 2 μm in the example of a particle having dimensions of 2 μm×5 μm. With the volume ($V_p$) and the density ($D_p$) of the particle, the mass ($M_p$) may be found using:

$$M_p = V_p \times D_p$$

Using the mass of the particle, the mass of the first material covering the particle ($M_1$) may be found using:

$$M_1 = \frac{\frac{S_1}{100} \times D_1}{D_p} \times M_p$$

As stated above, the sum of all $M_1$ values for i=1 to n may then provide the mass of the first material in the sample of the lubricating fluid.

Referring back to FIG. 3A, at step 312, once the mass of the first material in the fluid sample (or per given unit of fluid) is obtained, a condition of the engine may be diagnosed. The condition may comprise a number of remaining flight hours for the engine, an expected need for engine maintenance, a level of impact of the coking on the engine, a reduction in efficiency of the engine (i.e. 10%, 25%, 50%, etc), and the like.

Table 1 below is an example lookup table that may be used for engine diagnosis, for example by the engine diagnosis system 112.

TABLE 1

| Coking per unit of sample fluid | Remaining Flight Hours before next maintenance |
| --- | --- |
| 0-5 mg/L | >500 hrs |
| 6-10 mg/L | 250-500 hrs |
| 11-15 mg/L | <250 hrs |

Table 2 below is another example lookup table that may be used for engine diagnosis.

TABLE 2

| Coking per unit of sample fluid | Level of impact of VA on the engine |
| --- | --- |
| 0-5 mg/L | Low |
| 6-10 mg/L | Medium |
| 11-15 mg/L | High |

More or less than three levels, as shown in Table 2, may be used. In addition, the values illustrated in Tables 1 & 2 and the ranges are only for illustrative purposes and should be not viewed as limiting.

Reference data may be used to establish the impact of the coking on the engine. For example, reference engines from a common engine family having run a certain number of hours using a given lubricating fluid may be analyzed to obtain the reference data. In some embodiments, the reference data is presented as one or more averages for all reference engines. The reference engines used for the reference data may form part of a common family with the engine under analysis. An engine family may be defined by any engine characteristic, such as type, model, operating principle, configuration, use, performance, thrust, torque, speed, power, etc. An engine family may also be defined by two or more engine features. For example, a family may correspond to turboprop engines, or turboprop engines in use in aircraft, or turboprop engines in use in aircraft and weighing between 150 and 450 kg. In another example, a family may correspond to a specific model or series, such as the PT-6 Series from Pratt & Whitney Canada. In some embodiments, a family may comprise sub-families, i.e. the family has at least one common engine characteristic and each sub-family has at least one additional common engine characteristic. Various combinations may be used.

In some embodiments, the reference data is presented as a percentage of selected engines matching one or more events. For example, out of 50 reference engines selected, i.e. comprising a similar level of coking per sample of lubricating fluid, the reference data may be presented as: 100% operated 200 hours without any problems, 91% operated 500 hours without any problems, 73% operated 600 hours without any problems, 10% operated 750 hours without any problems. Other events may also be used in this format.

In some embodiments, diagnosing a condition of the engine, as per step 312, comprises assigning a rating to the engine. Various types of engine rating systems may be used, and comprise any number of rating levels, such as two, three, four, and more. The ratings may be associated with an expected time until maintenance, or an expected time until breakdown. The rating may be determined using only the reference data of the reference engines, or a combination of reference data of the reference engines and historical/current data of the engine under analysis. For example, if the expected time until maintenance is 600 hours, the probability of achievement will be 73% based on the reference engines. Other rating systems may readily apply.

In some embodiments, diagnosing a condition of the engine comprises determining a source of the coking in the engine. In particular, particles covered by the first material may be further analyzed to determine the nature of the other materials covering the surface of the particle. If a certain other alloy is dominant in the other materials, this may be indicative of coking coming from a component composed of the dominant alloy. The source of coking may be used to recommend a course of action, as a function of the source of coking and its potential impact on the engine. Components that are more critical may lead to an earlier maintenance while components that are less critical may lead to a later maintenance. Other implementations are also considered.

In some embodiments, the condition of the engine is used to determine whether an aircraft having an engine with a given level of coking should be deployed or not for a mission. In some embodiments, the method further comprises a step of taking a maintenance action based on the diagnosing, such as but not limited to issuing a report on the level of corrosion of the engine, setting a flag indicating a need for inspection, performing further inspection of the engine, and the like.

Figure 5:
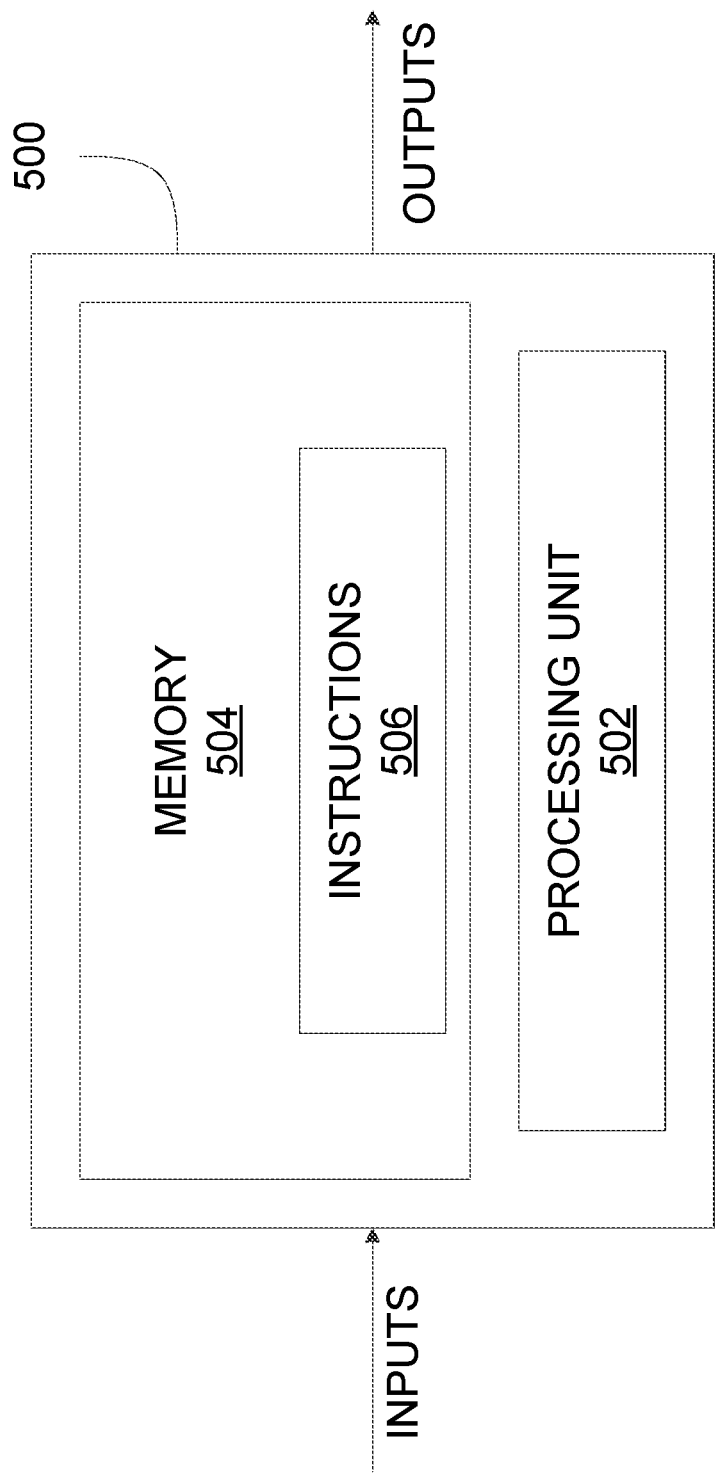
FIG. 5 is a block diagram of an example computing device for implementing a method for determining a level of coking in lubricating fluid, in accordance with some embodiments.

FIG. 5 is an example embodiment of a computing device 500 for implementing the engine diagnosis system 112 and/or the fluid analysis module 116 described above. The computing device 500 comprises a processing unit 502 and a memory 504 which has stored therein computer-executable instructions 506. The processing unit 502 may comprise any suitable devices configured to cause a series of steps to be performed such that instructions 506, when executed by the computing device 500 or other programmable apparatus, may cause the functions/acts/steps specified in the methods described herein to be executed. The processing unit 502 may comprise, for example, any type of general-purpose microprocessor or microcontroller, a digital signal processing (DSP) processor, a CPU, an integrated circuit, a field programmable gate array (FPGA), a reconfigurable processor, other suitably programmed or programmable logic circuits, or any combination thereof.

The memory 504 may comprise any suitable known or other machine-readable storage medium. The memory 504 may comprise non-transitory computer readable storage medium, for example, but not limited to, an electronic, magnetic, optical, electromagnetic, infrared, or semiconductor system, apparatus, or device, or any suitable combination of the foregoing. The memory 504 may include a suitable combination of any type of computer memory that is located either internally or externally to device, for example random-access memory (RAM), read-only memory (ROM), electro-optical memory, magneto-optical memory, erasable programmable read-only memory (EPROM), and electrically-erasable programmable read-only memory (EEPROM), Ferroelectric RAM (FRAM) or the like. Memory 504 may comprise any storage means (e.g., devices) suitable for retrievably storing machine-readable instructions 406 executable by processing unit 502. In some embodiments, the memory 504 stores one or more specific chemical composition for the first material associated with coking. In some embodiments, the memory 504 stores reference data from reference engines, and/or one or more lookup tables associating various levels of coking with corresponding engine conditions.

The methods and systems for diagnosing a condition of an engine and/or for determining a level of coking in a fluid sample as described herein may be implemented in a high level procedural or object oriented programming or scripting language, or a combination thereof, to communicate with or assist in the operation of a computer system, for example the computing device 500. Alternatively, the methods and systems for diagnosing a condition of an engine and/or for determining a level of coking in a fluid sample may be implemented in assembly or machine language. The language may be a compiled or interpreted language. Program code for implementing the methods and systems for diagnosing a condition of an engine and/or for determining a level of coking in a fluid sample may be stored on a storage media or a device, for example a ROM, a magnetic disk, an optical disc, a flash drive, or any other suitable storage media or device. The program code may be readable by a general or special-purpose programmable computer for configuring and operating the computer when the storage media or device is read by the computer to perform the procedures described herein. Embodiments of the methods and systems for diagnosing a condition of an engine and/or for determining a level of coking in a fluid sample may also be considered to be implemented by way of a non-transitory computer-readable storage medium having a computer program stored thereon. The computer program may comprise computer-readable instructions which cause a computer, or more specifically the processing unit 502 of the computing device 500, to operate in a specific and predefined manner to perform the functions described herein.

Computer-executable instructions may be in many forms, including program modules, executed by one or more computers or other devices. Generally, program modules include routines, programs, objects, components, data structures, etc., that perform particular tasks or implement particular abstract data types. Typically the functionality of the program modules may be combined or distributed as desired in various embodiments.

The above description is meant to be exemplary only, and one skilled in the art will recognize that changes may be made to the embodiments described without departing from the scope of the invention disclosed. Still other modifications which fall within the scope of the present invention will be apparent to those skilled in the art, in light of a review of this disclosure.

Various aspects of the methods and systems for detecting a fault may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments. Although particular embodiments have been shown and described, it will be obvious to those skilled in the art that changes and modifications may be made without departing from this invention in its broader aspects. The scope of the following claims should not be limited by the embodiments set forth in the examples, but should be given the broadest reasonable interpretation consistent with the description as a whole.

The invention claimed is:

1. A method for diagnosing a condition of an aircraft engine, the method comprising:
    obtaining a sample of lubricating fluid from the engine;
    filtering the sample to obtain a plurality of particles from the lubricating fluid;
    directing an excitation beam towards the particles;
    detecting an energy level emitted from the particles in response to the excitation beam;
    determining a level of coking in the lubricating fluid based on a difference between the energy level as detected and an expected energy level; and
    diagnosing a condition of the engine based on the level of coking in the lubricating fluid.

2. The method of claim 1, wherein determining the level of coking in the lubricating fluid comprises:
    determining a percentage of surface area of the particles covered by a first material based on the difference between the energy level as detected and the expected energy level, the first material resulting from coking; and
    determining the level of coking in the lubricating fluid based on the percentage of surface area covered by the first material.

3. The method of claim 2, wherein determining the level of coking in the lubricating fluid based on the percentage of surface area covered by the first material comprises:
    determining a quantity of the first material per particle; and summing the quantity of the first material per particle of all particles having the first material.

4. The method of claim 3, further comprising determining if particles having the first material also have a third material associated with coking, and wherein determining the level of coking in the lubricating fluid comprises considering only particles having the first material and the third material.

5. The method of claim 4, wherein the first material is carbon and the third material is phosphorous.

6. The method of claim 3, wherein determining the quantity of the first material per particle comprises:
   determining a percentage of surface area of the particles covered by at least one second material; and
   estimating a mass of the first material per particle.

7. The method of claim 6, wherein estimating the mass of the first material per particle comprises:
   determining a particle density based on the percentage of surface area covered by the first material, the percentage of surface area covered by the at least one second material, a density of the first material, and a density of the at least one second material; and
   estimating the mass of the first material based on the percentage of surface area covered by the first material and the particle density.

8. The method of claim 1, wherein directing an excitation beam towards the particles comprises directing energy dispersive x-rays.

9. The method of claim 1, wherein directing an excitation beam towards the particles comprises directing light.

10. A system for diagnosing a condition of an engine, the system comprising:
    at least one processor; and
    a memory having stored thereon program code executable by the at least one processor for:
    directing an excitation beam towards a plurality of particles filtered from a sample of lubricating fluid obtained from the engine;
    detecting an energy level emitted from the particles in response to the excitation beam;
    determining a level of coking in the lubricating fluid based on a difference between the energy level as detected and an expected energy level; and
    diagnosing a condition of the engine based on the level of coking in the lubricating fluid.

11. The system of claim 10, wherein determining the level of coking in the lubricating fluid comprises:
    determining a percentage of surface area of the particles covered by a first material based on the difference between the energy level as detected and the expected energy level, the first material resulting from coking; and
    determining the level of coking in the lubricating fluid based on the percentage of surface area covered by the first material.

12. The system of claim 11, wherein determining the level of coking in the lubricating fluid based on the percentage of surface area covered by the first material comprises:
    determining a quantity of the first material per particle; and
    summing the quantity of the first material per particle of all particles having the first material.

13. The system of claim 12, wherein the program code is further configured for determining if particles having the first material also have a third material associated with coking, and wherein determining the level of coking in the lubricating fluid comprises considering only particles having the first material and the third material.

14. The system of claim 13, wherein the first material is carbon and the third material is phosphorous.

15. The system of claim 12, wherein determining the quantity of the first material per particle comprises:
    determining a percentage of surface area of the particles covered by at least one second material; and
    estimating a mass of the first material per particle.

16. The system of claim 15, wherein estimating the mass of the first material per particle comprises:
    determining a particle density based on the percentage of surface area covered by the first material, the percentage of surface area covered by the at least one second material, a density of the first material, and a density of the at least one second material; and
    estimating the mass of the first material based on the percentage of surface area covered by the first material and the particle density.

17. The system of claim 10, wherein directing an excitation beam towards the particles comprises directing energy dispersive x-rays.

18. The system of claim 10, wherein directing an excitation beam towards the particles comprises directing light.

* * * * *